(12) United States Patent
Sun et al.

(10) Patent No.: US 8,983,165 B2
(45) Date of Patent: Mar. 17, 2015

(54) SYSTEM AND METHOD FOR MEASURING X-RAY BEAM PROFILE USING AN AREA DETECTOR

(75) Inventors: Mingshan Sun, Sunnyvale, CA (US);
Josh Star-Lack, Palo Alto, CA (US);
Gary Virshup, Cupertino, CA (US);
Daniel Morf, Buck am Irchel (CH);
Stefan Jochem Thieme-Marti, Windisch (CH)

(73) Assignee: Varian Medical Systems, Inc., Palo Alto, CA (US)

(*) Notice: Subject to any disclaimer, the term of this patent is extended or adjusted under 35 U.S.C. 154(b) by 998 days.

(21) Appl. No.: 13/070,067

(22) Filed: Mar. 23, 2011

(65) Prior Publication Data

US 2012/0014618 A1 Jan. 19, 2012

Related U.S. Application Data

(60) Provisional application No. 61/365,204, filed on Jul. 16, 2010.

(51) Int. Cl.
| | |
|---|---|
| *G06K 9/00* | (2006.01) |
| *G01D 18/00* | (2006.01) |
| *G12B 13/00* | (2006.01) |
| *G01T 1/24* | (2006.01) |
| *H01L 25/00* | (2006.01) |
| *H01L 27/00* | (2006.01) |
| *H01L 27/146* | (2006.01) |

(Continued)

(52) U.S. Cl.
CPC .............. *A61B 6/4266* (2013.01); *A61B 6/582* (2013.01); *A61B 6/5205* (2013.01); *A61N 5/1075* (2013.01); *A61B 2019/524* (2013.01); *A61B 2017/00725* (2013.01); *A61N 2005/1061* (2013.01)
USPC ............... 382/132; 378/4; 378/197; 378/207; 250/252.1; 250/370.09; 600/407

(58) Field of Classification Search
None
See application file for complete search history.

(56) References Cited

U.S. PATENT DOCUMENTS 8,199,873 B2 * 6/2012 Star-Lack et al. ................ 378/7
8,199,879 B2 * 6/2012 Star-Lack et al. ............ 378/98.4

(Continued)

OTHER PUBLICATIONS

Schmidgunst, C. and Ritter, D. and Lang, E., "Calibration model of a dual gain flat panel detector for 2D and 3D x-ray imaging", Medical Physics, 34, 3649-3664 (2007), DOI:http://dx.doi.org/10.1118/1.2760024.*

(Continued)

*Primary Examiner* — Randolph I Chu
*Assistant Examiner* — Nathan Bloom (57) ABSTRACT

The claimed subject matter describes a novel technique to measure the beam profile using an area detector. In one embodiment, a set of one-dimensional beam profile measurements is performed by taking two images under the same source conditions but at two different positions of the detector, with each position of the detector shifted by a certain distance in the direction corresponding to the direction of the one-dimensional profile measurement. In further embodiments, a set of two-dimensional beam profile measurements is achieved by determining a second set of one-dimensional profiles from the same sampling points in a second direction and building a two-dimensional map of the beam profile by correlating the first one-dimensional profile measurement with the second one-dimensional profile measurement.

30 Claims, 9 Drawing Sheets

(51) Int. Cl.
*A61B 6/00* (2006.01)
*G01N 23/00* (2006.01)
*G21K 1/12* (2006.01)
*H05G 1/60* (2006.01)
*H05G 1/02* (2006.01)
*A61N 5/10* (2006.01)
*A61B 5/05* (2006.01)
*A61B 19/00* (2006.01)
*A61B 17/00* (2006.01)

(56) References Cited

U.S. PATENT DOCUMENTS

| 8,326,011 | B2* | 12/2012 | Star-Lack et al. | 382/131 |
| 2002/0021758 | A1* | 2/2002 | Chui | 375/240.19 |
| 2007/0065038 | A1* | 3/2007 | Maschauer et al. | 382/274 |
| 2009/0274272 | A1* | 11/2009 | Stanton et al. | 378/62 |
| 2010/0308229 | A1* | 12/2010 | Bertram et al. | 250/363.04 |
| 2011/0228906 | A1* | 9/2011 | Jaffray et al. | 378/65 |
| 2012/0041685 | A1* | 2/2012 | Ding et al. | 702/19 |
| 2012/0140875 | A1* | 6/2012 | Dennerlein et al. | 378/19 |
| 2013/0058458 | A1* | 3/2013 | Desaute | 378/62 |

OTHER PUBLICATIONS

Yongjian Yu; Jue Wang, "Beam hardening-respecting flat field correction of digital X-ray detectors," Image Processing (ICIP), 2012 19th IEEE International Conference on , vol., No., pp. 2085,2088, Sep. 30, 2012-Oct. 3, 2012.*

Maltz, J.S.; Gangadharan, B.; Bose, S.; Hristov, D.H.; Faddegon, B.A.; Paidi, A.; Bani-Hashemi, A.R., "Algorithm for X-ray Scatter, Beam-Hardening, and Beam Profile Correction in Diagnostic (Kilovoltage) and Treatment (Megavoltage) Cone Beam CT," Medical Imaging, IEEE Transactions on , vol. 27, No. 12, pp. 1791,1810, Dec. 2008.*

Star-Lack, Josh, et al. "Efficient scatter correction using asymmetric kernels." SPIE Medical Imaging. International Society for Optics and Photonics, Mar. 2009.*

Overdick, Michael, Torsten Solf, and Hans-Aloys Wischmann. "Temporal artifacts in flat dynamic x-ray detectors." Medical Imaging 2001. International Society for Optics and Photonics, 2001.*

* cited by examiner

Exemplary Computer System 900

Figure 9

SYSTEM AND METHOD FOR MEASURING X-RAY BEAM PROFILE USING AN AREA DETECTOR

CLAIM OF PRIORITY

This application claims priority to the provisional application entitled, "System and Method for Measuring X-Ray Beam Profile Using Area Detector," filed Jul. 16, 2010, Application No. 61/365,204.

TECHNICAL BACKGROUND

The usage of area x-ray beams is common in the field of x-ray imaging and external radiation treatment to generate images of a target volume. For many imaging applications, a beam of x-rays or other radiation particles is directed from a radiation source and through a target volume or object. The traversing particles of the beam are collected in an imager or detector positioned on the far side of the target volume with respect to the source, and the data acquired by the acquisition (reception) of the particles in the imager may be subsequently used to generate an image of the target volume.

Certain characteristics of the particular beam used in acquiring the images are also critical to many applications, and may have a significant impact on the quality of the images and the treatment generated by the X-ray beams. For example, many digital X-ray imaging applications which include conventional scatter correction and dose verification techniques require knowledge of the spatial distribution of the flux intensity (also known as the beam profile) of the radiation beam used during the application. In addition, the beam profile data can also be used to facilitate calibration for X-ray detectors (e.g., gain calibration), and flat panel detectors in particular. Unfortunately, the generation of non-uniform beam fields is common in many radiology and medical imaging devices. This non-uniformity, when not properly calibrated for, can cause unintended artifacts in generated images which may significantly impact the quality of a generated image.

Non-uniformity of the beam field can be attributed to a variety of factors which include non-uniform directionality of Brehmsstrahlung radiation and the varying attenuation properties of the x-ray tube components (e.g. the Heel effect) and its associated housing. Ideally, in an ideal imager where the detector pixels each have a uniform response, the beam profile should approximate a flood field image (e.g., no object in the path of the beam). In practice however, practically all detectors also have gain variations caused by inherent imperfections in the sensors and the associated electronic circuitry. These gain variations must be calibrated out to create images that are sufficiently uniform and artifact-free. Unfortunately, conventional gain calibration techniques also remove flux intensity variations. Thus, after calibration, the flood field measurement will be a uniform signal, rendering any information regarding flux intensity variations lost.

One conventional approach of determining the beam profile involves performing a raster scan of the beam field with a small (e.g., single point) detector, determining the flux intensity of the beam at each designated point, and subsequently combining the results to form the beam profile. However, this approach suffers from several significant drawbacks: the scanning mechanism is cumbersome and the measurement time required is often lengthy since many beam pulses are required. Moreover, geometric pointing inaccuracies and global flux intensity variations from scan-to-scan can limit the accuracy of the final result. Another conventional method of determining the beam profile is by measuring the beam field using a large area of a detector. While more time-efficient than using a single point of a detector, the inherent non-uniformity among one or more pixels of the x-ray detector can detrimentally affect the accuracy of a beam profile thus measured.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in traditional beam calibration methods, a new technique for measuring the beam profile is herein provided. This technique uses an area detector to generate two or more spatially correlated images, and mathematically decouples the detector gain profile from the beam profile yielding relative flux intensity variations.

The claimed subject matter describes a novel technique to measure the beam profile using an area detector. No special requirement is needed for the detector and without requiring prior calibration. In one embodiment, the technique comprises generating two images from an area detector, deriving one or more sets of one-dimensional beam profile measurements from the generated images, and decoupling measured gain effects and flux intensity measurements from the sets of one-dimensional beam profiles, thereby advantageously providing a simple and relatively quick process to perform beam calibration. The technique provides a method of generating a beam profile for the x-ray field and a gain profile for the detector, which can used to properly calibrate the detector such as if the field were flat.

In one embodiment, a set of one-dimensional beam profile measurements is performed by taking two images under the same source conditions but at two different positions of the detector, with each position of the detector shifted by a certain distance in the direction corresponding to the direction of the one-dimensional profile measurement. In further embodiments, a set of two-dimensional beam profile measurements is achieved by determining a second set of one-dimensional profiles from the same sampling points in a second direction and building a two-dimensional map of the beam profile by correlating the first one-dimensional profile measurement with the second one-dimensional profile measurement.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 2 and 3) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other computing devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Exemplary Radiation Treatment and Imaging Machine

Figure 1:
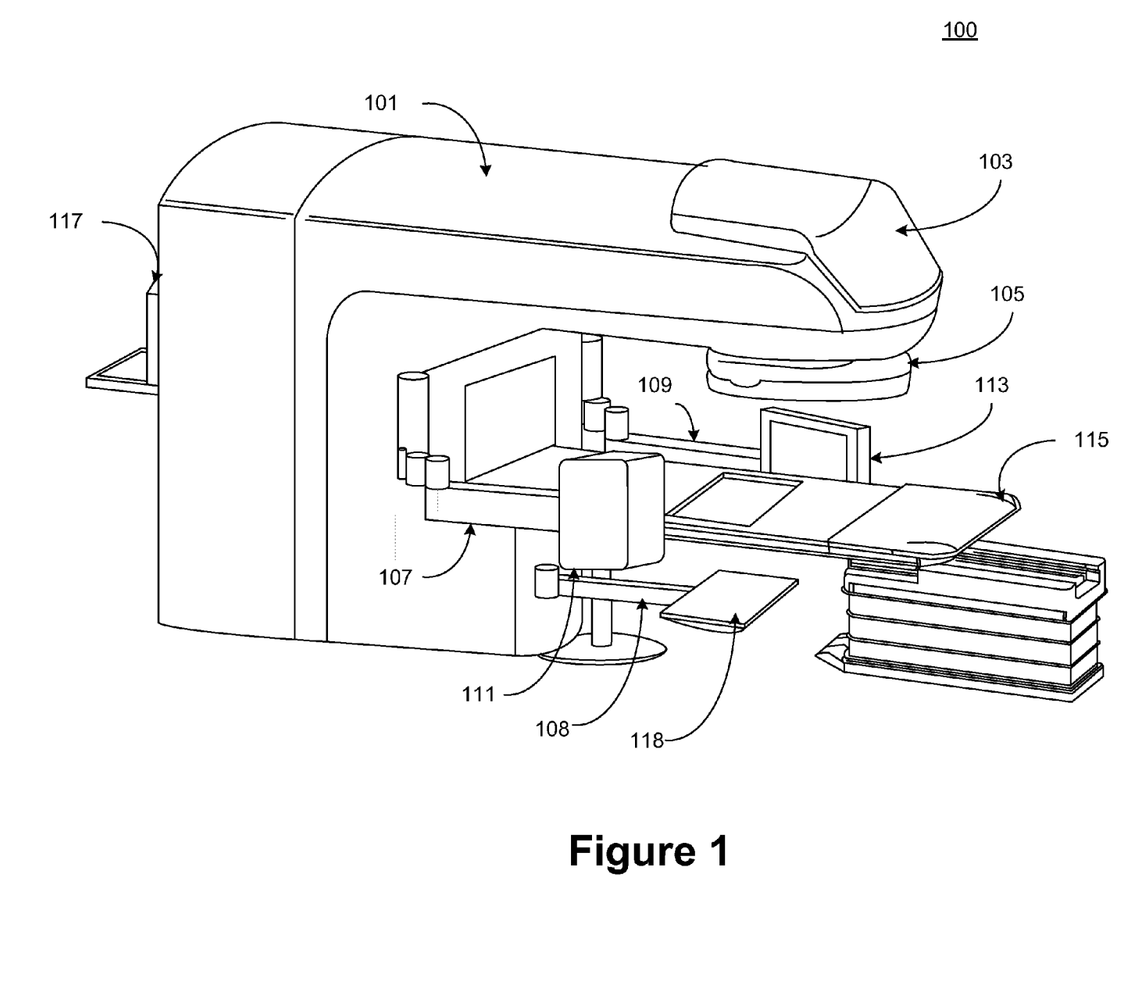
FIG. 1 depicts an illustration of an exemplary radiation therapy and imaging device, in accordance with embodiments of the present invention.

With reference now to FIG. 1, an illustration of an exemplary radiation therapy and imaging device 100 is depicted, in accordance with one embodiment. In one configuration, radiation therapy and imaging device 100 includes a support structure (e.g., gantry 101), and a radiation source 103 (e.g., a medical or clinical linear accelerator) including a treatment head 103. In one embodiment, the treatment head 103 receives a primary electron beam (e.g., from an electron gun), which will then hit a target material (commonly consisting of a high-Z metal), after which the electrons will produce what are referred to as "bremsstrahlung photons," and thereby generating a photon beam, ultimately emanating from a treatment source 105.

In further embodiments, a plurality of robotic arms (e.g., robotic arms 107, 108 and 109) may be attached to the gantry and coupled to a second (diagnostic) radiation source 111, and an area detector panel 113 (typically comprising a grid of single point detectors). According to some embodiments, an additional arm may be attached to a portal area detector panel 118 for receiving radiation from the treatment source 105. In still further embodiments, the device 100 may also include a patient couch 115. The radiation therapy and imaging device 100 may further include a communicatively coupled computing device 117 for processing images and/or controlling and manipulating the device 100. According to some embodiments, radiation emanating from the treatment source 105 and received in the portal area detector panel 118 may operating in the range of mV radiation (mega-voltage radiation), whereas radiation distributed from the second radiation source 111 and received in the area detector panel 113 may operate in the range of kV radiation (kilo-voltage).

In one embodiment, the end of gantry 101 positioned above patient couch 115 is attached to a radiation source 105 used to generate radiation (e.g., for therapeutic or imaging purposes). A patient is positioned (typically supine) on patient couch 115. A target volume (generally disposed within or about the patient subject) is irradiated by transmitting a radiation beam (e.g., X-ray photon beam) through the target volume and receiving the beam in the area detector panel 113 from source 111 or detector panel 118 from source 105. According to one embodiment, an image of the target volume can be acquired using either the diagnostic source 111 or therapeutic radiation source 105 in conjunction with either the area detector 113 or area detector 118, respectively. In alternate embodiments, x-ray detectors and radiation sources may be used for diagnostic and other applications that are not related to the radiotherapy field.

Certain parameters of the device 100 may be calibrated to produce or emphasize certain qualities of generated images. These parameters may include, for example, modifying the intensity or angle of the photon beam, and/or position of area detector 113 or area detector 118. However, due to the inherent variances in flux intensity of the generated photon beam and gain variances among the single point detectors within the area detector, the image generated by such a device may suffer from undesirable effects which may reduce the image quality. According to one aspect of the present claimed subject matter, a method is provided for measuring the beam profile by using the area detector panel 113 in conjunction with a radiation imaging source 111 to generate two or more spatially correlated images, and mathematically decoupling the detector gain profile from the beam profile yielding relative flux intensity variations derived from the correlated images, thereby allowing a more efficient calibration of the imaging device 100 and enabling the production of artifact-free images. Similarly this could be done with source 105 and detector 118.

In other embodiments, the system may not include a radiation therapy device. Instead, the system may consist of a radiation source and an imager. For example, in other embodiments, the system may include an x-ray source and a flat panel detector. In further embodiments, the source and imager may or may not be mounted on a rotational gantry. While embodiments are described herein to comprise the generation and usage of X-ray (photon) beams, it is to be understood that alternate embodiments are well suited for the generation and use of other particles and corresponding particle beams. These alternate embodiments may include, but are not limited to, electrons and electron beams; protons and proton beams; and ions and ion beams.

Beam Profile Measurement

Figure 2:
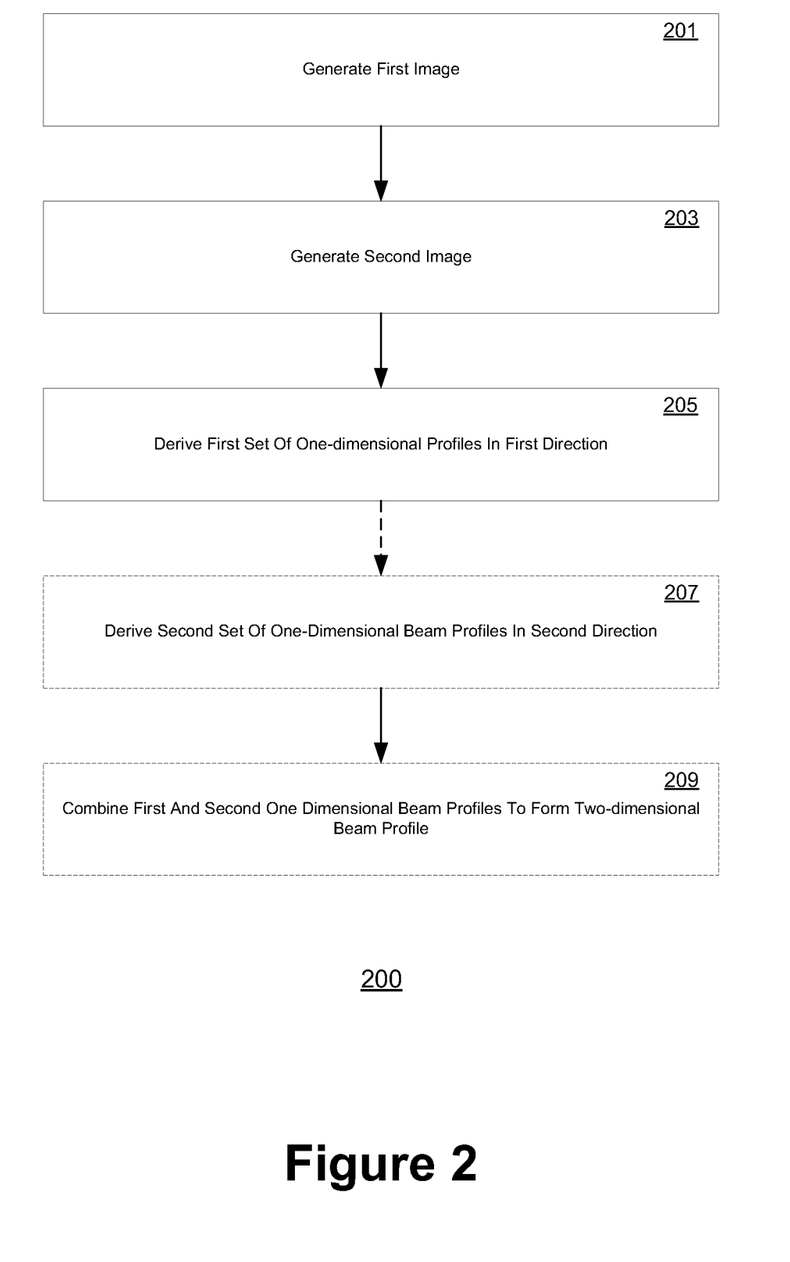
FIG. 2 depicts a flowchart of a method for measuring the beam profile of a photon beam, in accordance with embodiments of the present invention.

FIG. 2 is a flowchart 200 of one embodiment of a method for measuring the beam profile of a photon beam, in accordance with one embodiment. In one embodiment, the method generates one dimensional sets of beam profile and gain measurements. In further embodiments, the method may be used to generate a two-dimensional map of a beam profile for a beam field and a gain map for a corresponding area detector, thereby enabling the efficient calibration of a photon beam generated in a radiation imaging device. This calibration advantageously provides a way to calibrate the imaging device to account for variances in the gain profile and flux intensity within the area detector and beam source, respectively, without requiring user-intensive and time consuming manipulation of individual single point detectors. Steps 201-209 describe exemplary steps comprising the process depicted in flowchart 200 in accordance with the various embodiments herein described. In one embodiment, the flowchart 200 is implemented as computer-executable instructions stored in a computer-readable medium.

At step 201, a first image of a target volume is generated. Generating the first image may be performed by, for example, receiving photons of a photon beam emitted by a beam source of an imaging device in an area detector of the imaging device at a first position. In one embodiment, the photon beam is a beam of X-rays, and the image is acquired by directing the stream of radiation through the target volume and collecting the photon particles in the area detector positioned on the other side of the target volume from the x-ray source, such that the target volume is interposed between the source and detector. The data collected from the arrangement of the particles in the detector may be subsequently used to generate an image of the target volume.

The photon beam may be generated by, for example, applying an electron beam (e.g., generated by an electron gun and accelerated via an accelerating device in a medical linear accelerator) to a metal target (e.g., consisting of a high-Z metal) and generating a beam of bremsstrahlung photons. In further embodiments, once the photon beam has been generated, the beam may be modified by passing the beam through a configuration of modulating and/or particle monitoring devices. Typically, one or more flattening filters, wedges, collimators may be implemented to refine (e.g., attenuate) the photon beam before application to the subject volume (patient).

At step 203, a second image of the target volume is generated with the area detector positioned at a second position which is not the equivalent of the first position. In still further embodiments, each of the first and second images may be spatially correlated. That is, each image may be displaced from other images by a specific, pre-determined distance and in a desired dimension (e.g., horizontally or vertically). According to some embodiments, the photon beam may also be generated according to a plurality of conditions (e.g., beam source conditions). These conditions may include, but are not limited to, generally customizable conditions such as the angle of the beam relative to the target volume and/or area detector, the area of the incident beam, distance from the beam source to the area detector, etc. According to one embodiment, the source conditions under which the beam source generates the photon beams used to acquire the first and second images may be consistent (i.e., equivalent). In still further embodiments, the area detector used to receive the photons of the photon beam may be implemented as a grid (matrix) or two dimensional array of single point detectors, each detector operable to generate at least one pixel in a generated image.

At step 205, a first set of one dimensional beam profile measurements is derived from the first and second image and oriented in a first direction (dimension) which corresponds to the direction of the displacement of the second image from the first. In some embodiments, the set of one-dimensional beam profiles may be derived by determining a first set of regions of interest in the first image, determining a second and corresponding set of regions of interest in the second image and acquiring data measurements for the data points corresponding to each of the regions of interest. These regions of interest may correspond to one or more single point detectors (and therefore, one or more pixels in an image). In some embodiments, the regions of interest in each image may comprise a plurality of regularly spaced regions of interest oriented in a single direction (dimension). In these cases, at least some of the regions of interest are separated in the said single direction by the specified displacement between the first and the second images. Data measurements from these regions of interest for each image may be used to provide a data point as a reference with which a set of one dimensional beam profiles of the beam field and the gain of corresponding pixels in an area detector may be derived.

For example, for a detector operating within a typical linear response range, the non-gain-calibrated output of the detector is proportional to the incident x-ray beam intensity, and (for exemplary purposes) may be expressed as:

$$ADU_{i,j} = g_{i,j} \cdot \int_{Pixel(i,j)} I_0(x, y) dx dy, \quad (1)$$

where $I_0(x,y)$ is the photon flux at the location (x,y) on the detector plane, which is then integrated over the area of the detector pixel (i,j); $ADU_{i,j}$ is the detector output value (analog-to-digital units) at the detector pixel (i,j); and the conversion and proportionality factor $g_{i,j}$ is the intrinsic gain of the pixel (i.e. detector element). The indices i and j range from 1 to the maximum size of the detector matrix in the x and y directions.

With gain calibration, the intrinsic proportionality factor $g_{i,j}$ is multiplied by another quantity $gc_{i,j}$ imposed by the gain calibration:

$$ADU_{i,j} = (gc_{i,j} \cdot g_{i,j}) \cdot \int_{Pixel(i,j)} I_0(x, y) dx dy, \quad (2)$$

where $gc_{i,j}$ represents an artificial scaling factor to scale the detector output, usually aimed to compensate for the non-uniformity in $g_{i,j}$, so that when a uniform field irradiates the detector, a uniform image is output by the detector. Equation (1) can be considered a special case of Eq. (2), where $gc_{i,j}$ is set to 1. The detector gain obtained by the measurement technique described here is a collective measure of the detector response including the intrinsic gain (g) and the gain calibration (gc), if any.

Rewriting the above expression in a fully discrete format with renamed variables provides the following expression:

$$I_m(i,j) = g(i,j) \cdot I_0(i,j), \quad (3)$$

where $I_0(i,j)$ is the flux intensity that an ideal detector with uniform gain would measure at the pixel (i,j), $I_m(i,j)$ is the measured intensity, and $g(i,j)$ is the total gain, which includes the intrinsic detector gain plus any software-based calibrations that have previously been included. Accordingly, a means of finding the relative gain g of each detector element (i,j) and the relative flux intensity $I_0$ at all positions in the radiation field is thereby provided.

For the sake of simplicity, the problem is presented in a single dimension. A first intensity measurement $I_{m1}$ is made with the detector in the "home" or first position. For element i, the measured signal intensity is the product of that element's gain g(i) and the x-ray flux intensity at position $I_0(i)$ $$I_{m1}(i) = g(i) \cdot I_0(i). \quad (4)$$

Note, while the elements are numbered i=1 to N where N is the total number of detector pixels in a row, other notations are suitable. Element 1 is the leftmost element and element N is the rightmost element.

A second measurement $I_{m1}$ is subsequently performed with the detector shifted to the right. For the special case of the shift being exactly one element, the element i−1 will be at the location in what was position i for the first measurement. Thus, the second measurement may be expressed as:

$$I_{m2}(i-1) = g(i-1) \cdot I_0(i), \quad (5)$$

Where $I_0(i)$ is the same flux intensity as in Eq. 4. Combining equations 4 and 5, the gain for element i can be written in terms of element i−1:

$$g(i) = \frac{I_{m1}(i)}{I_{m2}(i-1)} g(i-1). \quad (6)$$

The recursive relationship depicted in Equation 6 shows that the gain values for all the detector pixels can be expressed in terms of the gain of a single (reference) detector pixel. For the case where the reference element is first (leftmost) detector pixel, the gain for element i is:

$$g(i) = \frac{\prod_{n=2}^{i} I_{m1}(n)}{\prod_{n=1}^{i-1} I_{m2}(n)} g(1). \quad (7)$$

After the gain for each element is obtained, Equation 4 can be used to establish the spatially dependent beam profile $I_0(i)$:

$$I_0(i) = \frac{I_{m1}(i)}{g(i)}. \quad (8)$$

An alternative way of deriving the beam profile is from the perspective of a fixed detector pixel. The measured intensity for a given detector pixel (i) for measurement 1 and measurement 2, where again the detector is shifted 1 pixel, may be expressed using the following two equations:

$$\begin{cases} I_{m1}(i) = g(i) \cdot I_0(i) \\ I_{m2}(i) = g(i) \cdot I_0(i+1) \end{cases}. \quad (9)$$

Note $I_0(i)$ and $I_0(i+1)$ are the flux intensities at the locations of elements i and i+1, respectively, before the detector is moved (i.e. for measurement 1). Following the same reasoning shown above for calculating detector gains, a recursive relation for the incident intensity for element i is determined:

$$I_0(i+1) = \frac{I_{m2}(i)}{I_{m1}(i)} I_0(i) \quad (10)$$

and the flux intensity for element i relative to that at a fixed location (e.g., $I_0(1)$) may be expressed as:

$$I_0(i) = \prod_{n=1}^{i-1} \frac{I_{m2}(n)}{I_{m1}(n)} I_0(1). \quad (11)$$

The detector gain can be subsequently calculated from Eq. 8 to be:

$$g(i) = \frac{I_{m1}(i)}{I_0(i)}. \quad (12)$$

In summary, two sets of inter-related formulas (Eqs. 7, 8 and Eqs. 11, 12) have been shown for deriving the beam profile and the detector gains by taking two measurements with the detector shifted from measurement 1 to measurement 2. These formulas can be used separately, or together in an alternating order, pixel-by-pixel, to solve for the gains and flux intensities across the entire detector.

Note that the expressions in Eqs. (7) and (11) give the gain and intensity, respectively, at a given location (i) relative to that at the leftmost pixel, and thus the solution can be considered as going from left to right. Alternatively, these equations also can be expressed in terms of the gain and intensity at the rightmost pixel, in which case they are solved from right to left.

In addition, the shift may not be limited to just one pixel, nor necessarily an integer number of multiples of the pixel size. More importantly, random noise associated with the measurements from single pixels is also a consideration. Therefore, in some embodiments, the average from a group of pixels may be used to evaluate the quantities of $I_m$, $I_0$, and g. The detector shift may be chosen empirically, and ideally should be meaningfully large enough so the distance is sufficiently accurate and the averaging areas do not overlap, but not too large to leave only a very few sampling points and a large separation in between. One possible selection for the shift distance could be the ASIC width if there are a number of detector ASICs along the measuring direction. This way, the group of pixels that are averaged are within each ASIC thus avoiding averaging measurements that potentially have large differences.

Figure 4:
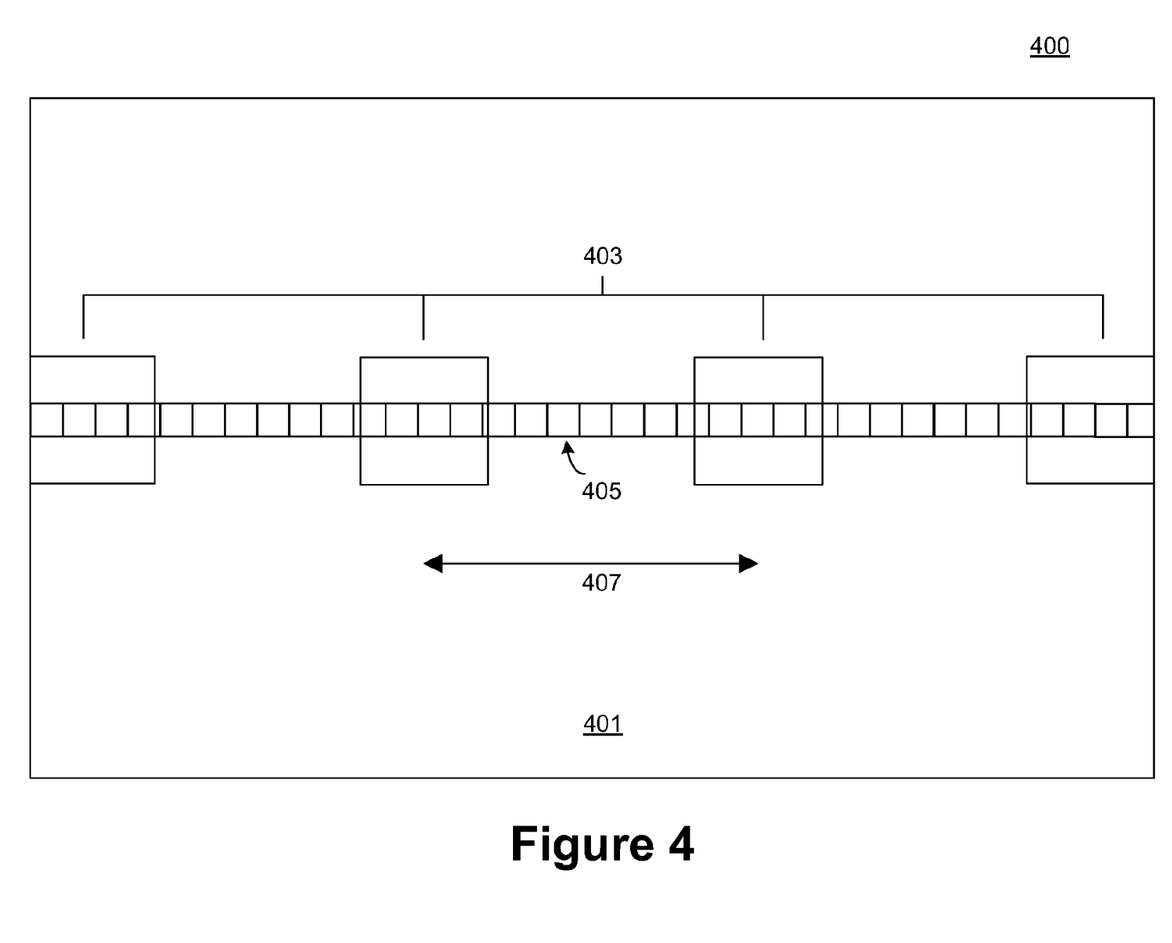
FIG. 4 is an illustration of an exemplary configuration of an area detector panel comprising a plurality of single point detectors, in accordance with embodiments of the present invention.

According to these embodiments, the calculation may be performed exactly the same as for the exemplary 1-pixel shift case and the same set of equations may be applied, with the caveat that pixel i and pixel i+1 are no longer two physically neighboring pixels (405), but two groups of pixels separated by the detector shift distance (407) (see FIG. 4). In still further embodiments, the distance of the first such group of pixels from the imager edge is another free variable and may be used to globally shift the sampling points on the detector plane. In the case that the x-ray field is larger than the detector in the measuring direction, the measurements at different locations may be repeated and the resultant gain profiles and the beam profiles may be subsequently combined together, to form a result covering the entire field. The combination can be done in the resultant gain and beam profile space, but also can be performed in the original detector image space. The latter case being effectively the equivalent of using a larger detector.

Step 205 thus provides a method for determining the gain at each pixel of an area detector as well as the beam profile at each space in a beam field corresponding to a set of one dimensional arrays of regularly spaced regions of interest. According to some embodiments, a two-dimensional beam profile and gain map may be subsequently achieved for the same two spatially correlated images by determining a second set of one-dimensional beam profiles at step 207 for the images in a separate direction (e.g., dimension) from the first set of one-dimensional beam profiles determined in step 205. The two sets of single-dimensional beam profiles can be correlated by selecting the same sampling points within the two images, thereby obtaining a full two dimensional map of the beam profile and detector gain at step 209.

The technique described above with reference to FIG. 2 can be used for various applications including improving scatter estimates for both radiographic and tomographic imaging, improving the accuracy of dose measurements during radiotherapy using an EPID, to characterize x-ray tube output, to facilitate flattening filter design, and for real time alignment of the electron beam in clinical linear accelerator (CLINAC) assembly. An accurate beam profile can also be used to aid beam hardening corrections where the heel effect is a factor by determining a map of the amount of target material being traversed by the radiation beam from the intensity drop across the detector, thereby providing accurate spectral information over the entire detection area. Being able to generate a detector gain map can also enable the study of detector gain variations by using the measured gain profile to perturb the gain calibration so that the output of the detector reflects the true incident flux intensity distribution. When a detector's gain is modified in this way, it frees up its dependence on the beam flux. The detector then measures the real time flux map and can be used in applications where a real time flux map is needed. An example is to help align the treatment beam in LINACs during assembly, by locating its peak output on the detector.

Decoupling Charge Trapping and Lag Effects

If not properly accounted for, the gain and beam profile measurements may be skewed by charge trapping effects in an imager made from amorphous silicon photo-diodes and transistors. Although gain changes may occur from frame to frame due to these effects, they can be substantially reduced by filling the traps as much as possible before the procedure starts. Alternatively, charge trapping effects can be mitigated by the following processing steps.

Starting with Eq. (9) above, the two measured intensities are:

$$\begin{cases} I_{m1}(i) = g(i) \cdot I_0(i) \\ I_{m2}(i) = g(i) \cdot (1 + \alpha I_{m1}) \cdot I_0(i+1) \end{cases} \quad (13)$$

For the second measurement, the gain g(i) is modified by factor given by 1+ a constant of proportionality ($\alpha$) multiplied by the first measurement $I_{m1}$. The constant $\alpha$ can be determined from a separate calibration step such as by taking two readings without moving the detector.

Following the same reasoning outlined in Eqs. (6) to (8), a recursive relation for the incident intensity may be expressed by the equation:

$$I_0(i+1) = \frac{I_{m2}(i)}{I_{m1}(i)} \cdot \frac{1}{1 + \alpha I_{m1}(i)} \cdot I_0(i) \quad (14)$$

and the intensity relative to that at any location (e.g., to $I_0(1)$):

$$I_0(i) = \prod_{n=1}^{i-1} \frac{I_{m2}(n)}{I_{m1}(n) \cdot (1 + \alpha I_{m1}(n))} I_0(1) \quad (15)$$

The detector gain is determined as shown in Eq. 12:

$$g(i) = \frac{I_{m1}(i)}{I_0(i)}. \quad (16)$$

The charge trapping in the photo diode is responsible for the lag and the gain effects. The lag effect—sometimes also referred to as ghosting—is caused by trapped charges that are released with a very slow time constant. The gain effect is primarily a result of the missing charge—the charges that get trapped—at the beginning of an exposure sequence. Some fraction of the charges gets trapped and cannot be read immediately, this effect appears as a reduced gain in the acquired image for earlier frames of a time sequence. As a result, the associated time constant may be disproportionately long compared to the frame read out time.

Figure 3:
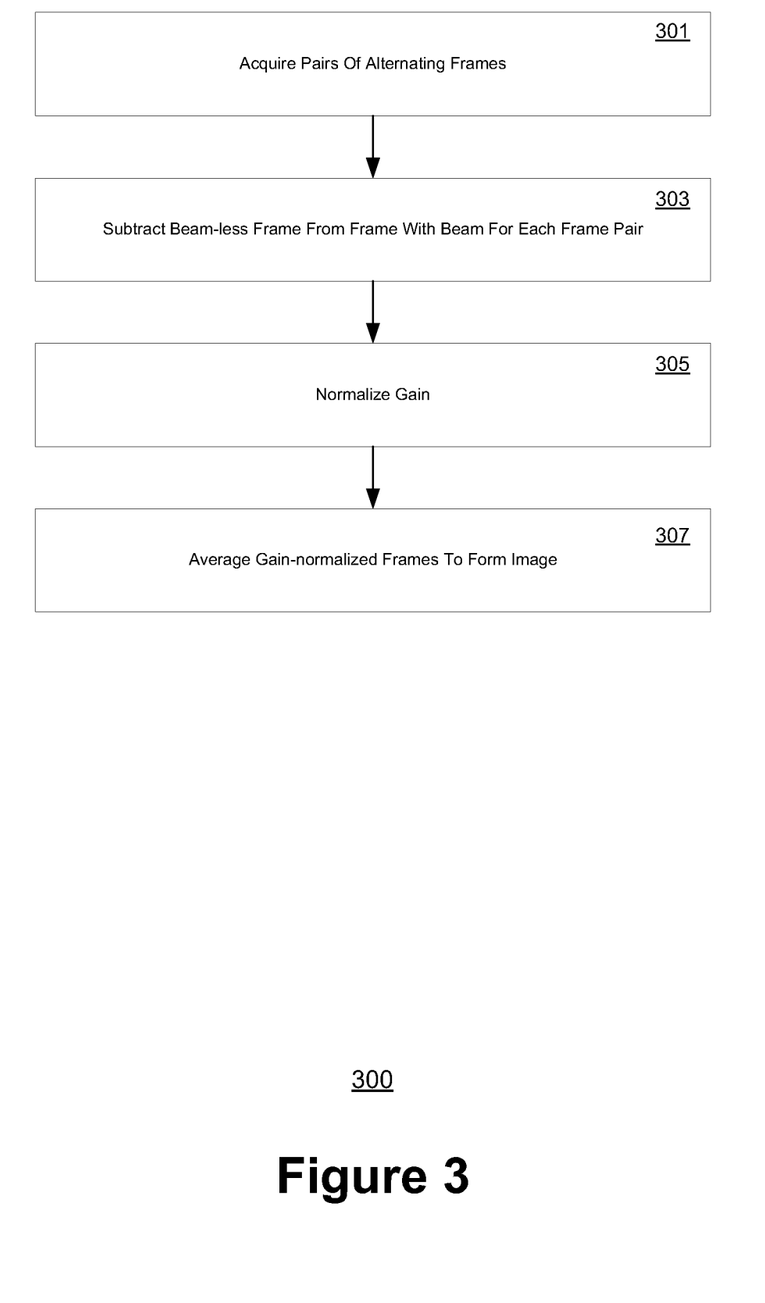
FIG. 3 depicts a flowchart of a method for minimizing trapped charge-induced errors during image acquisition, in accordance with one embodiment.

The behavior of the gain and the lag effects are very similar (but not identical), since they are caused by the same underlying physical effect, that is, the charge trapping. In order to minimize the errors caused by the trapped charge, and to reduce the reliance on Eqs. 13-16, an alternative image acquisition method is presented in FIG. 3. FIG. 3 depicts a flowchart 300 of one embodiment of a method for minimizing trapped charge-induced errors during image processing, in accordance with one embodiment. In one embodiment, the method enables the efficient correction of gain-defects due to the trapped charge effect in images. Steps 301-305 describe exemplary steps comprising the process depicted in flowchart 300 in accordance with the various embodiments herein described. In one embodiment, the flowchart 300 is implemented as computer-executable instructions stored in a computer-readable medium.

As presented in FIG. 3, at step 301, a sequence of frames comprising a target volume is generated by an imaging device. According to one embodiment, the sequence of frames comprises corresponding pairs of frames, wherein each pair of frames in the sequence of frames comprises a frame of the target volume with a generated radiation beam and a frame of the target volume without a generated radiation beam. According to some embodiments, the method described in FIG. 3 may be implemented with as few as two pairs of frames, and the sequence of frames may number as few as three frames. That is, a single exposure may be used as the first frame. The radiation beam may be implemented as a diagnostic radiation beam or a therapeutic radiation beam, according to various embodiments.

At step 305, the gain is normalized for each pair of frames. Normalizing the gain for each pair of frames may be achieved by, in one embodiment, deriving one-dimensional gain profiles or two-dimensional gain maps for both frames of each frame pair and subtracting the gain of the frame acquired without the radiation beam from the gain of the frame acquired with the radiation beam. The gain itself may be derived according to the methodology provided above with respect to FIG. 2. In another embodiment, the frame acquired without the radiation beam is subtracted from the frame acquired with the radiation beam. The resulting frame forms a first image. The imager is then shifted by a known distance, and the process is repeated to form a second image. The beam profile may be derived according to FIG. 2.

At step 307, the gain measurements from the gain-normalized frames obtained in step 305 are averaged to form a single image having as a set of gain measurements the average gain measurements of the sequence of frames. This is expressed by the following formula:

$$\text{Image} = \sum_{j=n-m-1}^{n} (\text{Frame}_{WithBeam}(j) - \text{Frame}_{WithoutBeam}(j))/m \quad (17)$$

Where n is the total number of acquired "frame pairs" and m is the number of frame pairs that are used for the calculation.

Once exposed to targeted radiation from a radiation source and after a period of idleness or disuse (e.g., overnight), an area detector may experience exponential increases in the effects of trapped charges that affect the measurements of detected gains. Over time and consistent (continuous) usage and exposure to radiation, the effects of the trapped charges level off. Accordingly, in some embodiments, the frames acquired during an initial period for a sequence of frames may be purged from consideration prior to the performance of step 303. Candidate frames for removal may comprise, for example, the frames acquired below a certain threshold of frames (e.g., 120 frames) or during an initial duration of time. In still further embodiments, instead of using a previous frame acquired without the radiation beam, a subsequent frame acquired without the radiation beam may be used to process the image. Also a single frame acquired without the beam could be used to process multiple frames acquired with the beam and multiple frames acquired without beam could be used to process a single frame acquired with beam. This method also corrects for other time variant errors such as, for instance, temperature related offset drifts or other slow changing image parameters.

Errors in measurements can propagate to the resulting beam profile and gain map. In particular, the overall pixel response and detector offset between acquired images may affect the accuracy of measurements. An equation which represents the relationship between two measurements with an offset vector $\Delta$ between measurements may be expressed as:

$$I_0(\vec{x} + \vec{\Delta}) = \frac{I_{m2}(\vec{x})}{I_{m1}(\vec{x})} I_0(\vec{x}) \quad (18)$$

In one embodiment, two measurements without spatial offset but with different source to imager distances are used to derive any exponential contribution due to an overall pixel response error. In another embodiment, two measurements without spatial offset but with rotations are used to find pixel response error. Any incorrect assumption with respect to the position change between the first and the second measurements leads to distorted beam profiles and detector gains. Thus, in still further embodiments, a generic correction function approximation by a bivariate power series is used with a plurality of measurements to account for the unknown overall pixel response and to correct the calculated gain.

Exemplary Area Detector Panel

Figure 5:
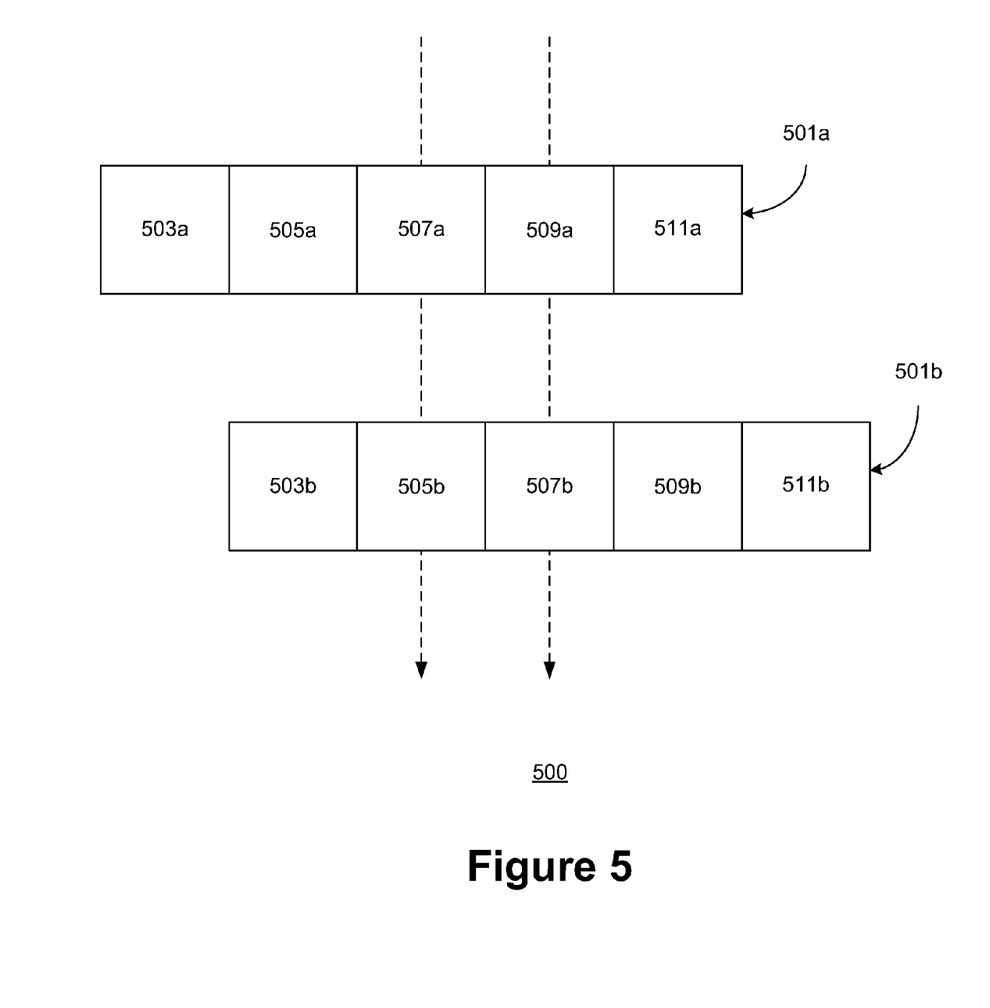
FIG. 5 depicts an illustration of an exemplary arrangement of single point detectors in an area detector panel, in accordance with embodiments of the present invention.

FIG. 4 is an illustration of an exemplary configuration 400 of an area detector panel 401 comprising a plurality of single point detectors 405. As depicted, the single point detectors 405 have been arranged as a single one dimensional array of detectors. However, according to alternate embodiments, the area detector panel 401 may be implemented as a two dimensional array (e.g., grid) of single point detectors spanning all or a significant portion of the area of the area detector panel 401. In some embodiments, a plurality of regions of interest 403 may be generated (e.g., by a computing device executing a process for deriving beam profile data) to correspond to one or more detectors 405 of the area detector panel 401. In further embodiments, the plurality of regions of interest 403 may be regularly spaced and separated by the detector shift distance. Note the distance of the first such group of pixels (e.g., leftmost region of interest 403) from the imager edge is another free variable and it can be used to globally shift the sampling points on the detector plane Exemplary Area Detector Panel Configuration FIG. 5 depicts an illustration of an exemplary arrangement of single point detectors in an area detector panel. For the sake of simplicity, an area detector panel (501a, 501b) is depicted in FIG. 5 as a single row or one dimensional array of single point detectors (e.g., 503a-511a and 503b-511b). Data measurements obtained by a row of single point detectors may be used in conjunction with a radiation beam field to obtain a set of beam profile measurements corresponding to a single dimension (in this case, the horizontal dimension) of a beam field as captured by an area detector. Alternate embodiments may be implemented as a multi-dimensional array or grid of detectors as described above. In one embodiment, an image may be generated with the area detector at a first position 501a in space. A subsequent or second image may be generated with the area detector at a second relative position 501b, offset in a corresponding orientation (e.g., horizontally) by a pre-determined distance.

As depicted in FIG. 5, the positions in space of one or more single point detectors of the area detector panel at the first position 501a may correspond to the positions in space of different single point detectors at the second position 501b. For example, as depicted, point detector 507a corresponds to point detector 505b, 509a corresponds to 507b, etc. According to such a configuration, the flux from the photons received at point detector 507a will be equivalent to the flux received at point detector 505b. Any changes from the total derived beam profile generated at that point detector, then, may be attributable to changes in the gain profile for the respective point detectors (507a, 505b).

Figure 6A:
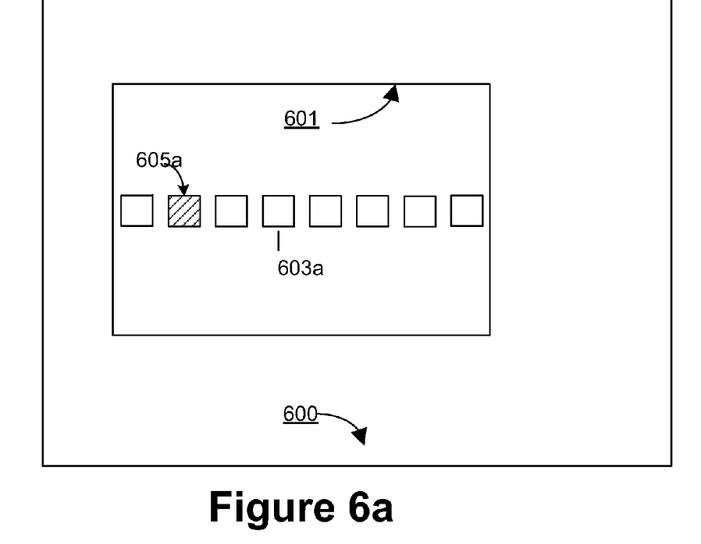
FIG. 6a depicts an illustration of an exemplary configuration of an area detector panel during a process for determining the gain profile of the area detector panel, in accordance with embodiments of the present invention.
Figure 6B:
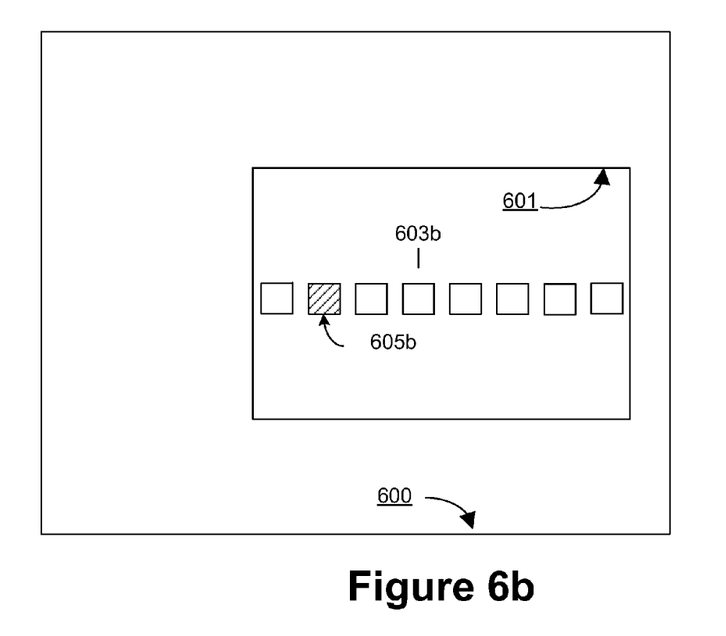
FIG. 6b depicts an illustration of an alternate exemplary configuration of an area detector panel during a process for determining the gain profile of the area detector panel, in accordance with embodiments of the present invention.

FIGS. 6a and 6b depict illustrations of exemplary configurations of an area detector panel 601, and sets of regions of interest 603a, 603b in a consistent beam field 600 during a process for determining the gain profile of the area detector panel. As depicted in FIGS. 6a and 6b, one or more regions of interest (605a, 605b) may correspond to the same position in space (e.g., the same position within the beam field 600) despite an incongruity in the relative position within the area detector panel 601.

In one embodiment, as presented in FIG. 6a, one or more regions of interest 605a in the set of regions of interest 603a may correspond to the same position in space as a region of interest 605b in the set of regions of interest 603b of FIG. 6b, despite an incongruity in the relative position within the respective area detector panel 601. Therefore, the pixels corresponding to the region of interest 605a in a first image generated with an area detector panel 601 at the indicated position of FIG. 6a will have a flux consistent with pixels corresponding to the region of interest 605b in a second image generated with the area detector panel 601 at the indicated position of FIG. 6b. And although the gain profile at the particular single point detectors corresponding in the regions of interest may vary as a result of inherent gain variance between the detectors comprising the area detector panel, since the only difference in the generated beam profile (e.g., image) data under these circumstances would be due to changes in the flux of the emitted photon beam, the gain profile for the respective single point detectors may be derived by factoring the derived constant flux from the acquired beam profile data by applying the methodology described above with respect to FIG. 2.

Figure 7A:
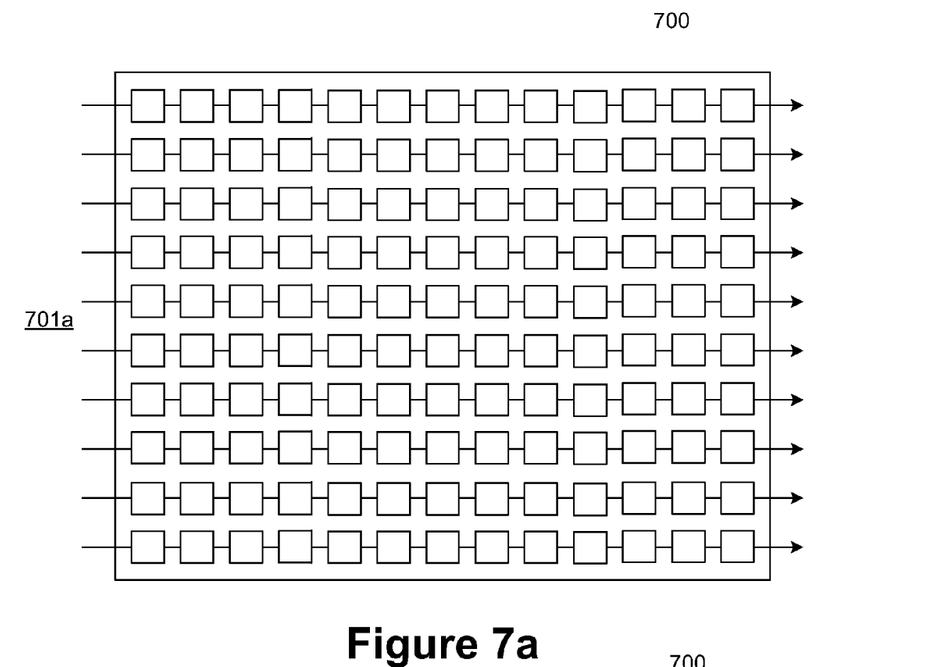
FIG. 7a depicts an illustration of an exemplary configuration of regions of interest in an area detector corresponding to a set of one-dimensional beam profile measurements, in accordance with embodiments of the present invention.
Figure 7B:
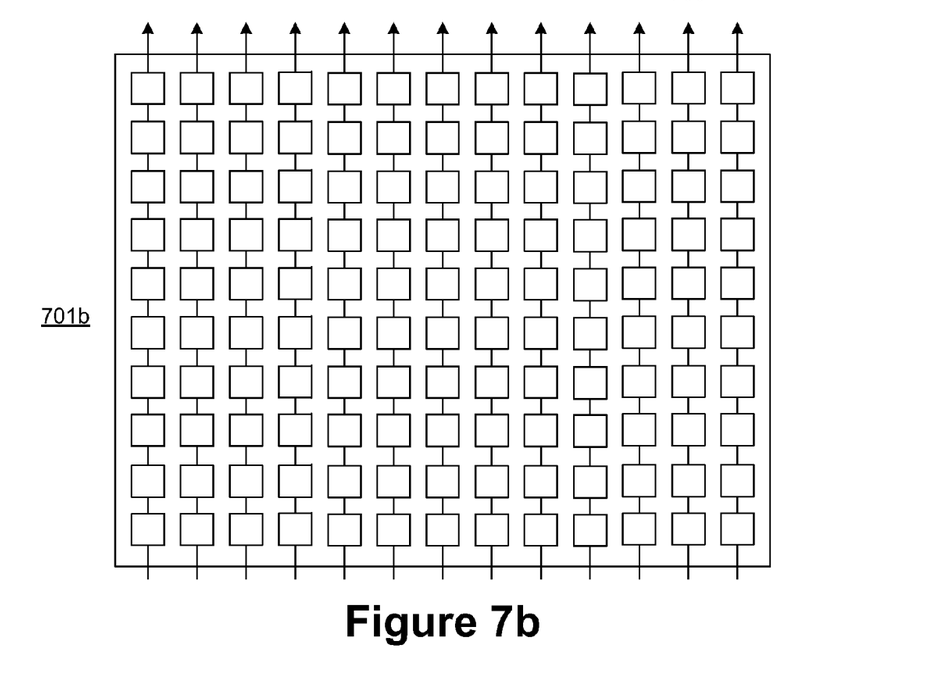
FIG. 7b depicts an illustration of an exemplary configuration of regions of interest in an area detector corresponding to a set of one-dimensional beam profile measurements, in accordance with embodiments of the present invention.

FIGS. 7a, and 7b, depict illustrations of exemplary configurations of regions of interest in an area detector corresponding to a set of one-dimensional beam profile measurements, in accordance with embodiments of the present invention. As depicted in FIGS. 7a and 7b, an area detector panel 700 may comprise a plurality of regions of interest 701a, 701b oriented in a given direction/dimension. As presented, the regions of interest (701a, 701b) are oriented horizontally in FIG. 7a, and vertically in FIG. 7b.

In one embodiment, a set of single-dimensional beam profile measurements as described above with respect to FIG. 2 may be acquired for the regions of interest in either the horizontal or vertical dimensions (FIGS. 7a, 7b, respectively). Each region of interest thus represents the combination of a pixel or group of pixels of an area detector with the area of a beam field in an incident beam, and the data acquired at each region of interest (as per step 205) comprises both the flux intensity of the beam as well as the gain.

Figure 8:
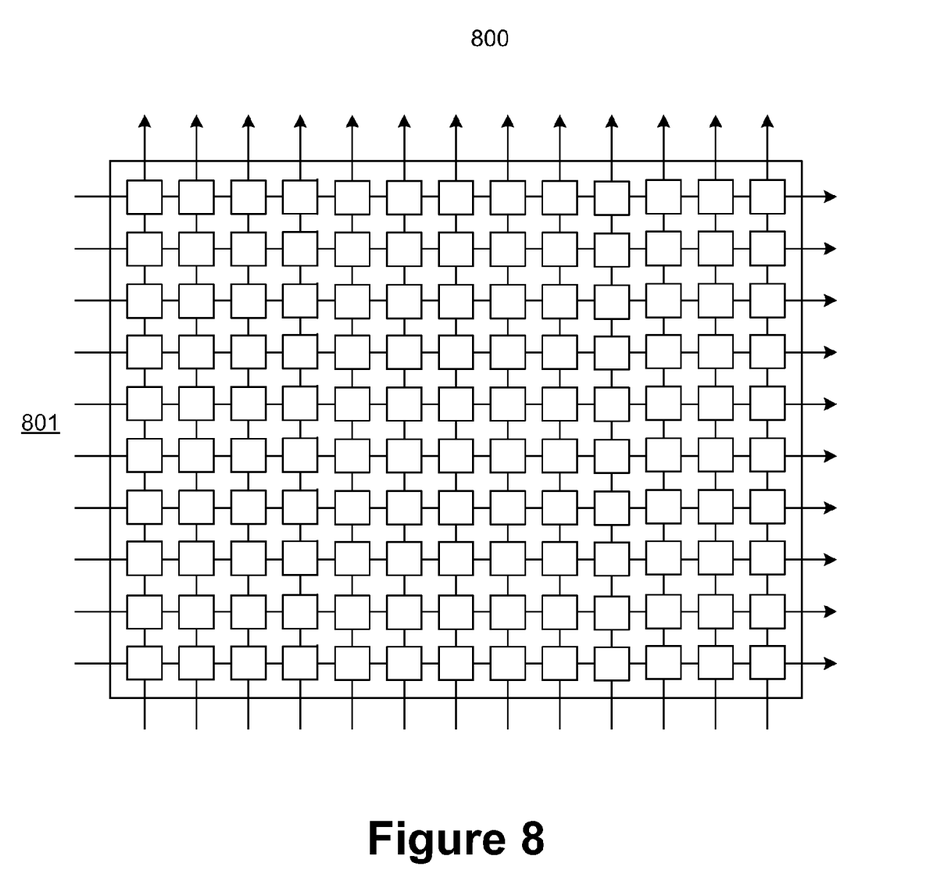
FIG. 8 depicts an illustration of an exemplary two dimensional map of beam profile measurements, in accordance with embodiments of the present invention.

FIG. 8 depicts an illustration of an exemplary two dimensional map of beam profile measurements, in accordance with embodiments of the present invention. As depicted in FIG. 8, the individual sets of one-dimensional beam profile measurements of FIGS. 7a and 7b described above have been merged to form a two dimensional map. Merging the individual sets of one-dimensional beam profile measurements may be achieved by, for example, selecting the same sample points as regions of interest in the individual sets of one-dimensional beam profile measurements and correlating the derived data.

In another embodiment, the spatially correlated images may be taken by rotating the imager. In this case, the beam profile and gain map are sampled in a set of circularly arranged regions of interest. According to a further embodiment, the spatially correlated images may be taken by moving the imager closer to or further from the radiation source. In still further embodiments, the spatially correlated images may be taken under any arbitrary but known position changes.

Exemplary Computing Device

Figure 9:
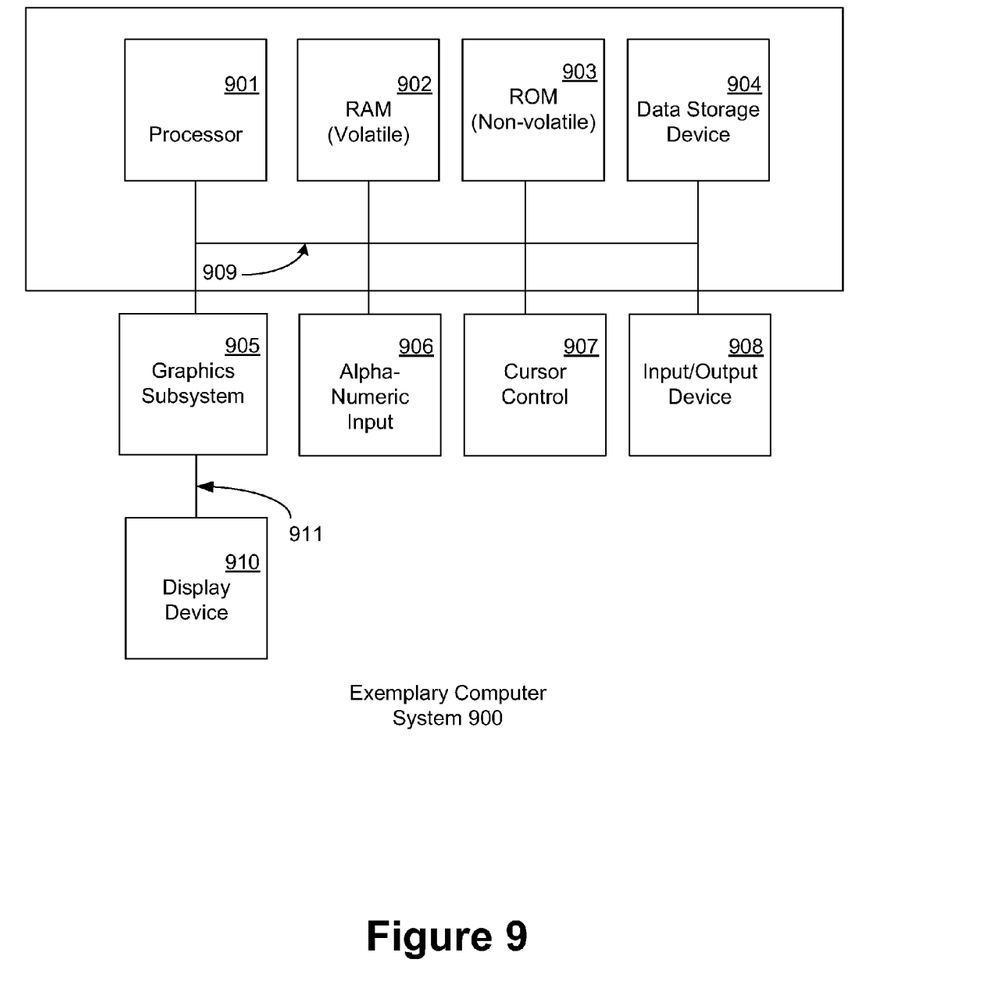
FIG. 9 depicts an exemplary computing environment, in accordance with embodiments of the present invention.

As presented in FIG. 9, an exemplary system upon which embodiments of the present invention may be implemented includes a general purpose computing system environment, such as computing system 900. In its most basic configuration, computing system 900 typically includes at least one processing unit 901 and memory, and an address/data bus 909 (or other interface) for communicating information. Depending on the exact configuration and type of computing system environment, memory may be volatile (such as RAM 902), non-volatile (such as ROM 903, flash memory, etc.) or some combination of the two.

Computer system 900 may also comprise an optional graphics subsystem 905 for presenting information to the computer user, e.g., by displaying information on an attached display device 910, connected by a video cable 911. According to embodiments of the present claimed invention, the graphics subsystem 905 may be coupled directly to the display device 910 through the video cable 911. A graphical user interface of an application for controlling a medical linear accelerator executing in the computer system 900 may be generated in the graphics subsystem 905, for example, and displayed to the user in the display device 910. In alternate embodiments, display device 910 may be integrated into the computing system (e.g., a laptop or netbook display panel) and will not require a video cable 911. In one embodiment, the processes 200 and 300 may be performed, in whole or in part, by graphics subsystem 905 in conjunction with the processor 901 and memory 902, with any resulting output displayed in attached display device 910.

Additionally, computing system 900 may also have additional features/functionality. For example, computing system 900 may also include additional storage (removable and/or non-removable) including, but not limited to, magnetic or optical disks or tape. Such additional storage is illustrated in FIG. 9 by data storage device 907. Computer storage media includes volatile and nonvolatile, removable and non-removable media implemented in any method or technology for storage of information such as computer readable instructions, data structures, program modules or other data. RAM 902, ROM 903, and data storage device 907 are all examples of computer storage media.

Computer system 900 also comprises an optional alphanumeric input device 906, an optional cursor control or directing device 907, and one or more signal communication interfaces (input/output devices, e.g., a network interface card) 909. Optional alphanumeric input device 906 can communicate information and command selections to central processor 901. Optional cursor control or directing device 907 is coupled to bus 909 for communicating user input information and command selections to central processor 901. Signal communication interface (input/output device) 909, also coupled to bus 909, can be a serial port. Communication interface 909 may also include wireless communication mechanisms. Using communication interface 909, computer system 900 can be communicatively coupled to other computer systems over a communication network such as the Internet or an intranet (e.g., a local area network), or can receive data (e.g., a digital television signal).

According to some embodiments, the computer system 900 may be communicatively coupled with an imaging device to derive beam profile information and enable the accurate and efficient calibration of an area detector panel and/or beam source. In still further embodiments, the computer system 900 may receive as data beam profile information collected from an imaging device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for measuring the beam profile of a generated radiation beam, the method comprising:
   generating a first image by receiving particles of a radiation beam in an area detector, the area detector being disposed at a first position;
   generating a second image by receiving particles of the radiation beam in the area detector at a second position, wherein the second position is offset from the first position in a first direction by a known distance;
   deriving a first set of one-dimensional beam profile measurements from the first and second image, the first one-dimensional beam profile measurements being oriented in the first direction;
   deriving a second set of one-dimensional beam profile measurements from the first and second image, the second set of one-dimensional beam profiles being oriented in a second direction; and
   correlating the first and second sets of one-dimensional beam profile measurements to form a two-dimensional beam profile map based on a selected a plurality of shared sampling points in the first and second images.

2. The method according to claim 1, wherein deriving a set of one-dimensional beam profile measurements comprises:
   determining a first set of regions of interest in the first image;
   determining a second set of regions of interest in the second image, the second set of regions of interest comprising a plurality of regions of interest offset from the plurality of regions of interest comprised in the first set of regions of interest in the first direction by the known distance; and
   acquiring a plurality of data points corresponding to first and second sets of regions of interest.

3. The method according to claim 2, wherein deriving a set of one-dimensional beam profile measurements further comprises:
   determining a relativity of a flux intensity of the radiation beam to a gain of the area detector for the plurality of data points;
   deriving a gain of the area detector corresponding to the plurality of data points; and
   decoupling the flux intensity of the radiation beam from the gain of the area detector for the plurality of data points.

4. The method according to claim 3, further comprising using the gain map to calibrate the area detector.

5. The method according to claim 3, wherein decoupling the flux intensity of the radiation beam from the gain of the area detector for the plurality of data points further comprises measuring a real time flux map from the flux intensity of the radiation beam.

6. The method according to claim 3, wherein the plurality of data points comprise data points in a single dimensional orientation.

7. The method according to claim 2, wherein the area detector comprises a grid of single point detectors, each single point detector of the grid of single point detectors being operable to generate a pixel comprised in an image generated by the area detector.

8. The method according to claim 7, wherein a region of interest corresponds to a plurality of single point detectors.

9. The method according to claim 7, wherein the first and second regions of interest comprise a least one common region of interest that corresponds to the same plurality of single point detectors of the grid of single point detectors.

10. The method according to claim 7, wherein the first and second regions of interest comprise a least one common region of interest that corresponds to the same position in space.

11. The method according to claim 2, wherein:
    the first set of regions of interest comprises a first plurality of regularly spaced regions of interest, and
    the second set of regions of interest comprises a second plurality of regularly spaced regions of interest.

12. The method according to claim 1 wherein the first image and the second image comprise an average of a plurality of images.

13. The method according to claim 12 wherein a process to reduce charge trapping effects and measurement errors is applied to the first and second images.

14. The method according to claim 13 wherein the process of reducing charge trapping effects and measurement errors further comprises the acquisition of a third image, wherein the third image is acquired at a different source-to-detector distance.

15. The method according to claim 1 wherein the radiation beam comprises a beam of particles, the beam of particles being comprised from at least one of the group of particles including: photons, electrons, protons, and ions.

16. The method according to claim 1 wherein the radiation beam comprises an X-ray beam.

17. The method according to claim 1, wherein the radiation beam comprises a photon beam emitted by a beam source under a set of source conditions.

18. The method according to claim 1, wherein the first image and the second image are generated under equivalent source conditions.

19. A system for measuring the beam profile of a radiation beam, the system comprising:
    an image generating device comprising a beam source operable to generate a radiation beam and an area detector operable to receive the radiation beam generated by the beam source; and a computer system having a processor coupled to a memory, the memory having computer readable code containing program instructions, the program instructions comprising:

instructions to generate a first image by receiving a first sequence of particles of a radiation beam emitted by the beam source in the area detector at a first position of the area detector;

instructions to generate a second image by receiving a second sequence of particles of a radiation beam emitted by the beam source in the area detector at a second position of the area detector;

instructions to derive a first set of one-dimensional beam profile measurements from the first and second image, the first set of one-dimensional beam profile measurements being oriented in a first direction;

instructions to derive a second set of one-dimensional beam profile measurements from the first and second image, the second set of one-dimensional beam profile measurements being oriented in a second direction; and instructions to correlate the first and second sets of one-dimensional beam profile measurements to form a two-dimensional beam profile map based on a selected a plurality of shared sampling points in the first and second images, wherein the second position is offset from the first position in the first direction by a known distance.

20. The system according to claim 19, wherein the program instructions further comprise:

instructions to determine a relativity of a flux intensity of the radiation beam to a gain of the area detector for a plurality of data points corresponding to a plurality of regions of interest in the first and second images;

instructions to derive a gain map of the area detector from the gain of the area detector corresponding to the plurality of data points; and instructions to decouple the flux intensity of the radiation beam from the gain of the area detector for the plurality of data points.

21. The system according to claim 20, wherein the gain map is used to calibrate the area detector.

22. The system according to claim 20, wherein the instructions to decouple the flux intensity of the radiation beam from the gain of the area detector for the plurality of data points comprises instructions to measure a real time flux map from the flux intensity of the radiation beam.

23. The method according to claim 20, wherein the plurality of data points comprise data points in a single dimensional orientation.

24. The system according to claim 19, wherein the area detector comprises a grid of single point detectors, each single point detector of the grid of single point detectors being operable to generate a pixel comprised in an image generated by the area detector.

25. The system according to claim 19, wherein the image generating device comprises a medical imaging device.

26. The system according to claim 25, wherein the image generating device comprises a radiation therapy device.

27. The system according to claim 19, wherein the beam profile measurement is used to calculate particle scatter estimates in a radiographic imaging procedure.

28. The system according to claim 27, wherein the radiographic imaging procedure comprises a cone-beam computer tomography (CBCT) imaging procedure.

29. The system according to claim 19, wherein the beam profile measurement is used to perform hardening corrections for the photon beam.

30. The system according to claim 19, wherein the radiation beam comprises a beam of particles, the beam of particles being comprised from at least one of the group of particles including: photons, electrons, protons, and ions.

* * * * *